US012796916B2

(12) United States Patent
Aibara

(10) Patent No.: US 12,796,916 B2
(45) Date of Patent: Nov. 17, 2026

(54) CHARACTERISTIC INSPECTION SYSTEM

(71) Applicant: FINDEX Inc., Tokyo (JP)

(72) Inventor: Teruo Aibara, Tokyo (JP)

(73) Assignee: FINDEX Inc., Tokyo (JP)

( * ) Notice: Subject to any disclaimer, the term of this patent is extended or adjusted under 35 U.S.C. 154(b) by 478 days.

(21) Appl. No.: 18/305,325

(22) Filed: Apr. 22, 2023

(65) Prior Publication Data

US 2023/0255477 A1 Aug. 17, 2023

Related U.S. Application Data

(63) Continuation-in-part of application No. PCT/JP2021/033444, filed on Sep. 13, 2021, which is (Continued)

(30) Foreign Application Priority Data

Jun. 16, 2020 (JP) ................................ 2020-103472
Aug. 25, 2020 (JP) ................................ 2020-141312
Nov. 5, 2020 (JP) ................................ 2020-184793

(51) Int. Cl.

| | |
|---|---|
| ***A61B 3/113*** | (2006.01) |
| ***A61B 3/00*** | (2006.01) |
| ***A61B 3/024*** | (2006.01) |

(52) U.S. Cl.

CPC .............. *A61B 3/113* (2013.01); *A61B 3/005* (2013.01); *A61B 3/0091* (2013.01); *A61B 3/024* (2013.01)

(58) Field of Classification Search

CPC ........ A61B 3/024; A61B 3/113; A61B 3/0091

(Continued)

(56) References Cited

U.S. PATENT DOCUMENTS 4,045,130 A * 8/1977 Krahn .................... A61B 3/024
351/233
5,035,500 A * 7/1991 Rorabaugh ............ A61B 3/024
351/224

(Continued)

FOREIGN PATENT DOCUMENTS

JP 2003-546 A 1/2003
JP 2011-161122 A 8/2011

(Continued)

OTHER PUBLICATIONS

Goseki T, Ishikawa H, Shoji N. Bilateral Concurrent Eye Examination with a Head-Mounted Perimeter for Diagnosing Functional Visual Loss. Neuroophthalmology. Sep. 20, 2016;40(6):281-285. doi: 10.1080/01658107.2016.1220593. PMID: 27928419; PMCID: PMC5120740. (Year: 2016).*

(Continued)

*Primary Examiner* — Zachary W Wilkes
(74) *Attorney, Agent, or Firm* — JTT Patent Services, LLC; Gerald T. Peters

(57) ABSTRACT

A characteristic testing system may comprise a line of sight detection unit, a target display unit, a visual recognition determination unit, and a characteristic testing unit. The line of sight detection unit may detect a line of sight of the user and output information pertaining to a direction of the line of sight. The target display unit may cause targets to be displayed. The visual recognition determination unit may carry out determination as to whether or not the user has visually recognized targets. The characteristic testing unit may control the target display unit and carry out testing with respect to the characteristic of the user based on movement of the line of sight when the targets are displayed. The characteristic testing unit may comprise a multiple target testing unit that carries out testing with respect to the (Continued)

characteristic of the user when a plurality of targets are simultaneously displayed.

7 Claims, 7 Drawing Sheets

Related U.S. Application Data a continuation-in-part of application No. PCT/JP2021/025184, filed on Jul. 2, 2021, which is a continuation-in-part of application No. PCT/JP2021/016860, filed on Apr. 27, 2021, application No. 18/305,325 is a continuation-in-part of application No. 18/173,724, filed on Feb. 23, 2023, now abandoned, which is a continuation-in-part of application No. 17/937,780, filed on Oct. 4, 2022, now abandoned, which is a continuation-in-part of application No. PCT/JP2021/016860, filed on Apr. 27, 2021, application No. 18/305,325 is a continuation-in-part of application No. 17/937,780, filed on Oct. 4, 2022, now abandoned, which is a continuation-in-part of application No. PCT/JP2021/016860, filed on Apr. 27, 2021.

(58) Field of Classification Search
USPC .................................................. 351/224, 237
See application file for complete search history.

(56) References Cited

U.S. PATENT DOCUMENTS

| | | | | |
|---|---|---|---|---|
| 5,737,060 | A | 4/1998 | Kasha, Jr. | |
| 5,880,812 | A * | 3/1999 | Solomon | A61B 3/024 351/209 |
| 5,946,075 | A * | 8/1999 | Horn | A61B 3/022 351/237 |
| 6,290,357 | B1 | 9/2001 | Massengill et al. | |
| 6,364,486 | B1 * | 4/2002 | Ball | A61B 3/024 351/203 |
| 6,367,932 | B1 * | 4/2002 | Donaldson | A61B 3/024 351/237 |
| 7,367,673 | B2 * | 5/2008 | McGrath | A61B 3/024 351/205 |
| 7,682,021 | B2 * | 3/2010 | Sabel | A61B 3/024 351/203 |
| 10,143,367 | B2 | 12/2018 | Gonzalez De La Rosa | |
| 10,178,949 | B2 | 1/2019 | Donaldson | |
| 10,772,113 | B2 | 9/2020 | Yerramalli et al. | |
| 11,116,393 | B2 * | 9/2021 | Liu | A61B 3/113 |
| 11,633,097 | B1 | 4/2023 | Ziff | |
| 12,161,410 | B2 | 12/2024 | Blaha | |
| 2003/0036907 | A1 | 2/2003 | Stewart et al. | |
| 2006/0114414 | A1 * | 6/2006 | McGrath | A61B 3/113 351/205 |
| 2009/0009714 | A1 | 1/2009 | Clarke et al. | |
| 2013/0155376 | A1 * | 6/2013 | Huang | A61B 3/024 351/224 |
| 2014/0340642 | A1 * | 11/2014 | You | A61B 3/18 351/246 |
| 2015/0199812 | A1 | 7/2015 | Hakoshima et al. | |
| 2016/0262613 | A1 * | 9/2016 | Klin | A61B 5/163 |
| 2017/0049316 | A1 | 2/2017 | Donaldson | |
| 2017/0245753 | A1 | 8/2017 | Donaldson | |
| 2017/0325677 | A1 | 11/2017 | Gonzalez De La Rosa | |
| 2018/0235466 | A1 | 8/2018 | Hakoshima | |
| 2018/0296084 | A1 | 10/2018 | Kawahara et al. | |
| 2019/0099072 | A1 | 4/2019 | Takii et al. | |
| 2019/0110678 | A1 * | 4/2019 | Liu | G16H 50/20 |
| 2019/0150727 | A1 | 5/2019 | Blaha | |
| 2019/0298166 | A1 * | 10/2019 | Smith | A61B 3/0091 |
| 2023/0023605 | A1 | 1/2023 | Aibara | |
| 2023/0190091 | A1 | 6/2023 | Aibara | |
| 2023/0309815 | A1 * | 10/2023 | Inoue | A61B 3/024 600/558 |
| 2024/0335104 | A1 | 10/2024 | Aibara | |

FOREIGN PATENT DOCUMENTS

| | | | | | |
|---|---|---|---|---|---|
| JP | 2016140423 | A | * | 8/2016 | A61B 3/00 |
| JP | 2017-176302 | A | | 10/2017 | |
| JP | 2017-529964 | A | | 10/2017 | |
| JP | 6606264 | B1 | * | 11/2019 | A61B 3/024 |
| JP | 2020-099556 | A | | 7/2020 | |
| JP | 2020-141848 | A | | 9/2020 | |
| JP | 2021-194289 | A | | 12/2021 | |
| JP | 2022-037273 | A | | 3/2022 | |
| JP | 2023-094652 | A | | 7/2023 | |
| WO | 2008 139137 | A1 | | 11/2008 | |
| WO | WO-2016007124 | A1 | * | 1/2016 | A61B 3/113 |
| WO | 2016 051136 | A1 | | 4/2016 | |
| WO | 2017 022757 | A1 | | 2/2017 | |
| WO | 2020 137544 | A1 | | 7/2020 | |
| WO | 2020 179351 | A1 | | 9/2020 | |
| WO | 2021 256100 | A1 | | 12/2021 | |
| WO | 2022 044548 | A1 | | 3/2022 | |
| WO | 2023 119913 | A1 | | 6/2023 | |

OTHER PUBLICATIONS

Jones PR, Smith ND, Bi W, Crabb DP. Portable Perimetry Using Eye-Tracking on a Tablet Computer—A Feasibility Assessment. Transl Vis Sci Technol. Feb. 5, 2019;8(1):17. doi: 10.1167/tvst.8.1.17. PMID: 30740267; PMCID: PMC6364754. (Year: 2019).*

International Search Report (ISR) and/or Written Opinion (WrOp), all apparently dated Jul. 13, 2021, in PCT/JP2021/016860, filed Apr. 27, 2021 and entitled "Visual Field Testing Apparatus", of which possibly related U.S. Appl. No. 17/937,780 is a bypass continuation-in-part.

International Search Report (ISR) and/or Written Opinion (WrOp), all apparently dated Sep. 21, 2021, in PCT/JP2021/025184, filed Jul. 2, 2021 and entitled "Visibility Determination System and Visual Field Test Apparatus", of which possibly related U.S. Appl. Nos. 17/937,780 and 18/173,724 are bypass continuations-in-part.

International Search Report (ISR) and/or Written Opinion (WrOp), all apparently dated Oct. 19, 2021, in PCT/JP2021/033444, filed Sep. 13, 2021 and entitled "Characteristic Inspection System", of which possibly related U.S. Appl. Nos. 17/937,780, 18/173,724, and 18/305,325 (i.e., the present application) are bypass continuations-in-part.

International Search Report (ISR) and/or Written Opinion (WrOp), all apparently dated Jan. 17, 2023, in PCT/JP2022/041472, filed Nov. 8, 2022 and entitled "Visual Field Testing Apparatus", of which possibly related U.S. Appl. Nos. 17/937,780, 18/173,724, 18/305,325 (i.e., the present application), and U.S. Appl. No. 18/743,015 are bypass continuations-in-part.

Testing of visual field with virtual reality goggles in manual and visual grasp modes, Dariusz Wroblewski, Jun. 23, 2014, Biomed Res Int., 2014, Jun. 23, 2014, 2014:206082, pp. 2-4, "2. Materials and Methods". Also see NPL Ref No. 4.

Head-mounted perimeter Aimo, Toshiaki Goseki, Mar. 25, 2017, Neuro-Ophthalmology Japan, vol. 34, No. 1, pp. 73-80, p. 74, right column, second paragraph, p. 79, left column, lines 9-3 from the bottom. NPL Ref No. 4 on the IDS off Jul. 9, 2025 submitted in lieu of translation.

Applicant brings to the attention of the Examiner the existence of possibly related U.S. Appl. No. 17/937,780 (inventor Teruo Aibara; assigned to FINDEX Inc.) filed Oct. 4, 2022 and published as US 2023 0023605 A1 on Jan. 26, 2023, which is a continuation-in-part of Intl App No. PCT/JP2021/016860 filed on Apr. 27, 2021 and published as WO 2021 256100 A1 on Dec. 23, 2021, and which has overlapping inventorship/ownership with the present case.

Applicant brings to the attention of the Examiner the existence of possibly related U.S. Appl. No. 18/173,724 (inventor Teruo Aibara; assigned to FINDEX Inc.) filed Dec. 23, 2023 and published as 2023

(56) References Cited

OTHER PUBLICATIONS

0190091 A1 on Jun. 22, 2023, which is a CIP of multiple applications including PCT/JP2021/025184 filed on Jul. 2, 2021 and published as 2022 044548 A1 on Mar. 3, 2022, and which has overlapping inventorship/ownership with the present case.
Applicant brings to the attention of the Examiner the existence of possibly related U.S. Appl. No. 18/743,015 (inventor Teruo Aibara; assigned to FINDEX Inc.) filed Jun. 13, 2024 and published as US 2024 0335104 A1 on Oct. 10, 2024, which is a CIP of multiple applications including PCT/JP2022/041472 filed on Nov. 8, 2022 and published as WO 2023 119913 A1 on Jun. 29, 2023, and which has overlapping inventorship/ownership with the present case.

* cited by examiner

CHARACTERISTIC INSPECTION SYSTEM

CROSS-REFERENCE TO RELATED APPLICATION(S), BENEFIT/PRIORITY CLAIM(S), AND INCORPORATION(S) BY REFERENCE

This application is a continuation-in-part of and claims benefit under 35 USC 120 and 365(c) to copending International Application No PCT/JP2021/033444, entitled "Characteristic Inspection System", filed 13 Sep. 2021; further is a continuation-in-part of and claims benefit under 35 USC 120 and 365(c) to International Application No PCT/JP2021/025184, entitled "Visibility Determination System and Visual Field Test Apparatus", filed 2 Jul. 2021, the aforesaid PCT/JP2021/025184 having been copending at the time of filing of the aforesaid PCT/JP2021/033444; further is a continuation-in-part of and claims benefit under 35 USC 120 and 365(c) to International Application No PCT/JP2021/016860, entitled "Visual Field Testing Apparatus", filed 27 Apr. 2021, the aforesaid International Application No PCT/JP2021/016860 having been copending at the time of filing of the aforesaid International Application No PCT/JP2021/025184; further is a continuation-in-part of and claims benefit under 35 USC 120 to copending U.S. patent application Ser. No. 18/173,724, entitled "Visibility Determination System and Visual Field Test Apparatus", filed 23 Feb. 2023, which is a continuation-in-part of and claims benefit under 35 USC 120 to copending U.S. patent application Ser. No. 17/937,780, entitled "Visual Field Testing Apparatus", filed 4 Oct. 2022, which is a continuation-in-part of and claims benefit under 35 USC 120 and 365(c) to the aforesaid International Application No PCT/JP2021/016860, the aforesaid U.S. patent application Ser. No. 17/937,780 having been copending at the time of filing of the aforesaid U.S. patent application Ser. No. 18/173,724, and the aforesaid International Application No PCT/JP2021/016860 having been copending at the time of filing of the aforesaid U.S. patent application Ser. No. 17/937,780; further is a continuation-in-part of and claims benefit under 35 USC 120 to the aforesaid U.S. patent application Ser. No. 17/937,780, which is a continuation-in-part of and claims benefit under 35 USC 120 and 365(c) to the aforesaid International Application No PCT/JP2021/016860, the aforesaid International Application No PCT/JP2021/016860 having been copending at the time of filing of the aforesaid U.S. patent application Ser. No. 17/937,780; further claims benefit of priority under 35 USC 119(a)-(d) to Japanese Patent Application No 2020-184793, entitled "Characteristic Inspection System", filed 5 Nov. 2020; further claims benefit of priority under 35 USC 119(a)-(d) to Japanese Patent Application No 2020-141312, entitled "Visibility Determination System and Visual Field Test Apparatus", filed 25 Aug. 2020; and further claims benefit of priority under 35 USC 119(a)-(d) to Japanese Patent Application No 2020-103472, entitled "Visual Field Testing Apparatus", filed 16 Jun. 2020, the contents of all of which applications are incorporated herein in their entireties by reference.

STATEMENT REGARDING PRIOR DISCLOSURES BY INVENTOR UNDER 37 CFR 1.77(b)(6)

The following patents and published patent applications are disclosures by, originating with, and/or attributable to the inventor of the present application:

WO 2021 256100 A1 ("Visual Field Testing Apparatus"; 23 Dec. 2021);
JP 2021 194289 A ("Visual Field Testing Apparatus"; 27 Dec. 2021);
WO 2022 044548 A1 ("Visibility Determination System and Visual Field Test Apparatus"; 3 Mar. 2022);
JP 2022 037273 A ("Visibility Determination System and Visual Field Test Apparatus"; 9 Mar. 2022);
WO 2022 097368 A1 ("Characteristic Inspection System"; 12 May 2022);
JP 2022 074616 A ("Characteristic Inspection System"; 18 May 2022); and
US 2023 0023605 A1 ("Visual Field Testing Apparatus"; 26 Jan. 2023).

FIELD OF THE INVENTION

The present invention relates to a characteristic testing system that carries out testing of user characteristics based on eye movement.

BACKGROUND

An apparatus in accordance with an embodiment of the present invention may carry out testing of user characteristics based on movements of the eye of the user. For example, at a visual field testing apparatus in accordance with one embodiment, the visual field of a user might be measured by causing the line of sight which is the direction in which the user is looking to be automatically detected by a line of sight detection apparatus, and by automatically determining whether or not the user sees a target.

furthermore, an apparatus in accordance with an embodiment of the present invention may use eye movement to detect user dementia or detect reduced cognitive function or the like due to depressed mental state.

At apparatuses that use targets to carry out testing of user characteristics, it may be that determination is carried out as to whether or not all of the targets which are sequentially displayed have actually been seen by the user. This may result in much time being required for testing of user characteristics, and this may place a large burden on the user during testing.

There is therefore a need to provide a characteristic testing system capable of efficiently testing user characteristics based on eye movement.

SUMMARY OF INVENTION

A characteristic testing system associated with one embodiment of the present invention may cause target(s) to be displayed at display(s) and may carry out testing of characteristic(s) of a user based on movement of line(s) of sight of the user.

Such a characteristic testing system may comprise a line of sight detection unit that detects line(s) of sight of the user and that outputs line of sight information pertaining to direction(s) of line(s) of sight.

In accordance with some embodiments, the characteristic testing system may further comprise a target display unit that causes target(s) to be displayed at display(s).

In accordance with some embodiments, the characteristic testing system may further comprise a visual recognition determination unit that carries out determination as to whether or not the user has visually recognized target(s) based on line of sight information and position information of target(s).

In accordance with some embodiments, the characteristic testing system may further comprise a characteristic testing unit that controls the target display unit and that carries out testing with respect to characteristic(s) of the user based on movement of line(s) of sight when target(s) are displayed.

In accordance with some embodiments, the characteristic testing unit may comprise a multiple target testing unit that carries out testing with respect to characteristic(s) of the user when a plurality of targets are simultaneously displayed at display(s).

At least some embodiments of the present invention make it possible to efficiently carry out testing of user characteristic(s) based on movement of line(s) of sight when a plurality of targets are displayed.

Other embodiments, systems, methods, and features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

EMBODIMENTS FOR CARRYING OUT INVENTION

Figure 1:
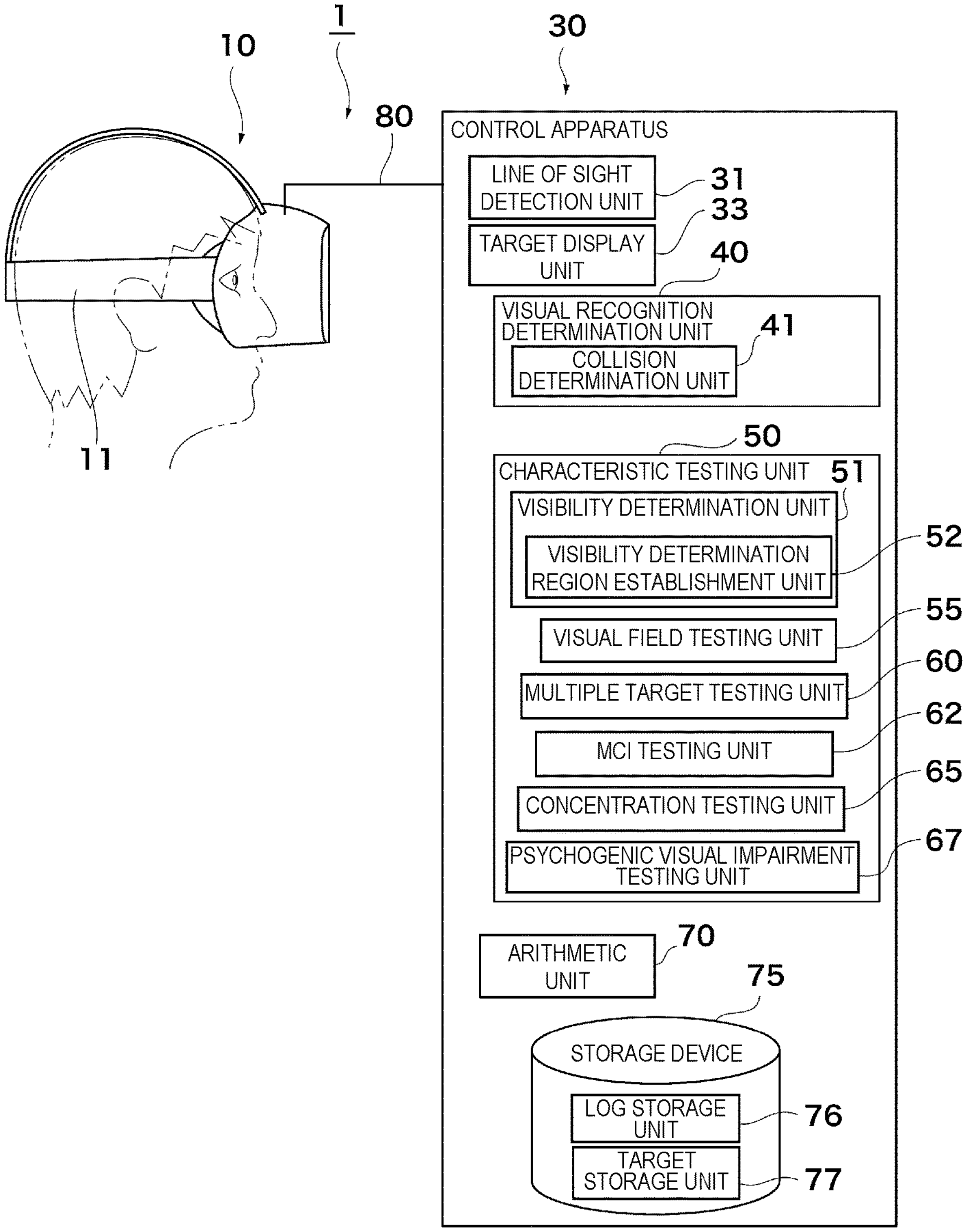
FIG. 1 is a schematic diagram showing in simplified fashion the constitution of a characteristic testing system associated with an embodiment of the present invention.
Figure 2:
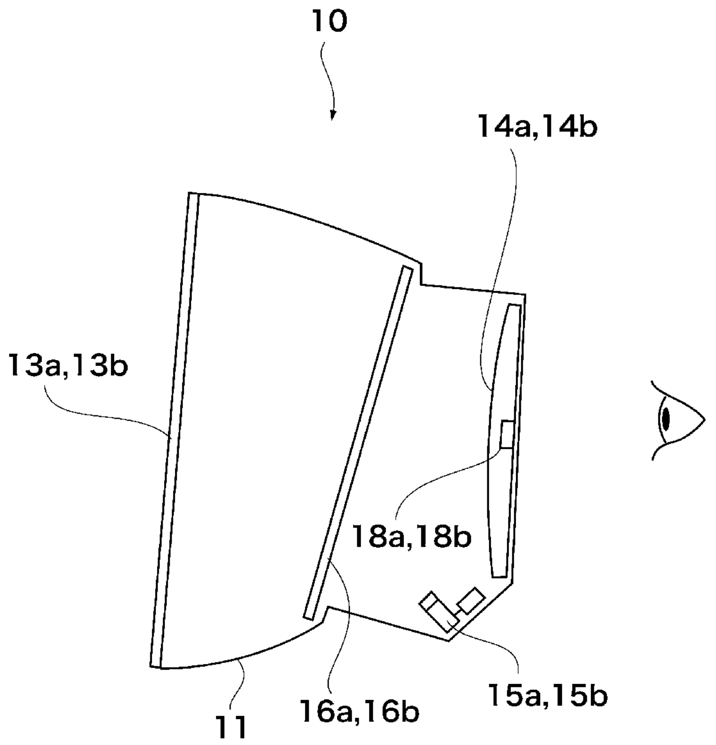
FIG. 2 is a sectional view of the principal components in, and showing in simplified fashion the constitution of, an HMD associated with an embodiment of the present invention.
Figure 3:
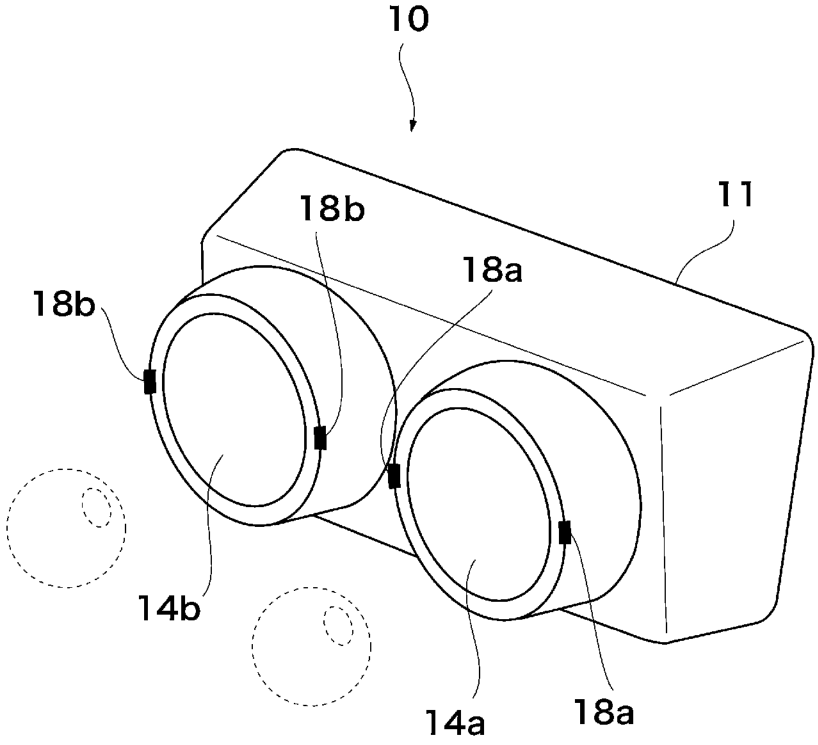
FIG. 3 is a perspective view of the principal components in, and showing in simplified fashion the constitution of, an HMD associated with an embodiment of the present invention.

Characteristic testing system 1, which is an embodiment of the present invention, will be described in detail hereinbelow with reference to the drawings. In accordance with one embodiment, characteristic testing system 1 automatically detects a line of sight which is a direction in which the eye(s) of a user are looking, and carries out testing of user characteristics based on movement of the line of sight at a time when target(s) are displayed. In accordance with the present embodiment, testing of user characteristic(s) is carried out as a plurality of targets are simultaneously displayed.

Characteristic testing system 1 in accordance with the present embodiment may comprise head mounted display (HMD) 10, control apparatus 30, and communication cable 80 which connects HMD 10 and control apparatus 30. HMD 10 may comprise case 11 which might include a belt for mounting thereof on the head of a user who is a test subject, display 13, convex lens 14, camera 15, hot mirror 16, and near-infrared emitter 18, and might be equipped with line of sight detection functionality for cooperating with line of sight detection unit 31, described below, to automatically detect a line of sight which is a direction in which the user on whom HMD 10 is mounted is looking with his or her eye(s).

Display 13 might be a liquid crystal display in which display 13*a* for the right eye of the user and display 13*b* for the left eye thereof are installed so as to respectively face the fronts of his or her left and right eyes. Respectively installed to the right and left between display 13 and the eyes of the user there may be convex lens 14*a* for the right eye and convex lens 14*b* for the left eye. Where this is the case, an image displayed at display 13 might be made to appear at the eye(s) of the user by way of convex lens 14.

Except where otherwise clear from context, note that use of the singular or plural herein should not be understood in a limiting or exclusionary sense where this would constitute an unreasonable interpretation of the present invention. For example, depending on the embodiment in question, it may be that both eyes are tested during a round of testing but only one eye is actively undergoing testing at any given moment. Likewise, depending on the embodiment in question, it may be that multiple sets of gazing targets and measurement targets are displayed during a round of testing but only one set, and more particularly only either the gazing target or the measurement target of that set, is actively being displayed at any given moment. Furthermore, depending on the embodiment in question, it may be that both eyes are tested but only one eye is being described by way of example. Moreover, as noted below, independent displays 13*a*, 13*b* may, for example, be used for the right eye and the left eye, or a single large display 13 that has been divided into a region 13*a* for the right eye and a region 13*b* for the left eye may be used, and depending on the embodiment in question the various units and other components for testing of the right eye and the left eye may similarly take the form of a single component for both eyes or separate components for each of the respective eyes. It should therefore be noted that regardless of whether the present specification makes reference in the singular to display 13, lens 14, camera 15, mirror 16, emitter 18, and so forth, or conversely makes reference in the plural to displays 13*a*, 13*b*, lenses 14*a*, 14*b*, cameras 15*a*, 15*b*, mirrors 16*a*, 16*b*, emitters 18*a*, 18*b*, and so forth, such references should except where otherwise clear from context be understood in a collective or nonexclusionary sense, without limitation as to whether there is a single such component for both eyes or separate components for the respective eyes. Similarly, references made herein to gazing target(s), measurement target(s), and the various apparatus (es) and unit(s) and so forth should, except where otherwise clear from context, be understood as nonlimiting with respect to number.

Camera 15 might be a near-infrared camera for capturing images of the eyes of the user, video capture of the left and right eyes of the user being carried out thereby through use of near-infrared light which is nonvisible light. Camera 15*a* for the right eye and camera 15*b* for the left eye might likewise be installed at camera 15.

Respectively installed to the right and left between display 13 and convex lens 14 there may be hot mirrors 16*a*, 16*b* having multilayer films which reflect near-infrared light and allow visible light to pass therethrough. Where this is the case, visible light of an image irradiated from display 13 might be made to pass through hot mirror 16, and near-infrared light which is nonvisible light that is irradiated from emitter 18 might be reflected by hot mirror 16.

Emitter 18 might be an LED (IR-LED) that causes near-infrared light to be irradiated as illumination for capturing images of the eyes of the user. Emitters 18*a*, 18*b* may respectively be installed to the left and right so as to face the left and right eyes of the user at the periphery of convex lens 14.

Camera 15 may be installed at the side toward the eyes, which is the side opposite display 13, from hot mirror 16. Near-infrared light which directly irradiates the eyes of the user from emitter 18 might be reflected by the eyes of the user and thereafter made to pass through convex lens 14 and be reflected by hot mirror 16 to arrive at camera 15 where an image might be captured therefrom.

Control apparatus 30 may comprise central processing unit(s) (CPU) or other such arithmetic unit(s) 70 for carrying out various types of operations, as well as hard disc drive(s) (HDD) for storing various types of information, and/or random access memory or memories (RAM) capable of being used as a work area during arithmetic processing, or other such storage device(s) 75.

Storage device 75 might comprise line of sight log storage unit 76 which records line of sight information that is output by line of sight detection unit 31, described below; and might further comprise target storage unit 77 which records target information to be displayed at display 13.

Furthermore, control apparatus 30 might comprise—in terms of functionalities—line of sight detection unit 31, target display unit 33, visual recognition determination unit 40, and/or visual field testing unit 50, these functionalities being implemented by causing prescribed program(s) stored at storage device 75 to be executed by arithmetic unit 70, for example.

Line of sight detection unit 31 might detect the direction in which the user is looking, i.e., the line of sight, based on captured image(s) of the eye(s) of the user as output by camera 15. After detecting the line of sight, line of sight detection unit 31 might output two angles θ, ϕ which are polar coordinates (spherical coordinates) as line of sight information (line of sight angles) that indicate the direction of the line of sight. In accordance with the present embodiment, taking a location at front and center to be the origin, the angle θ might, for example, be taken to indicate the angle (°) in the horizontal direction (lateral direction) from a line of sight directed toward the location at front and center (the origin), and the angle ϕ might, for example, likewise be taken to indicate the angle (°) in a perpendicular direction (vertical direction) from the location at front and center.

Establishment of a polar coordinate system such as the foregoing may be carried out during the calibration which might, for example, be made to take place prior to the start of visual field measurement. More specifically, the user might be made to stare at a previously designated target and the image thereof might be made to correspond to the polar coordinate system origin (center of eyeball), following which an image at which the user is made to stare at a point representing a different designated set of polar coordinates might be stored. By determining the correlation between the locations of the centers of the pupils captured in the respective images and the respective polar coordinates at which the user was made to stare, it is, for example, possible to determine the line of sight angles (θ, ϕ) within the polar coordinate system from the images.

In a preferred embodiment, this line of sight detection that is carried out by line of sight detection unit 31 is carried out independently for the right eye and the left eye, and it is preferred in accordance with the present embodiment that line of sight information be recorded as a function of time at line of sight log storage unit 76 at intervals of approximately 15 ms, for example. The aforementioned line of sight angles (θ, ϕ) might, for example, be included within the line of sight information which may be recorded at line of sight log storage unit 76 in accordance with the present embodiment.

Target display unit 33 may cause target(s) of prescribed size(s) to be displayed at prescribed locations(s) at display 13 based on target information recorded at target storage unit 77. At the target information stored at target storage unit 77, note that sets of the aforesaid two polar coordinate system angles θ, ϕ may be used as location information indicating display locations of respective targets, it being possible to define a target angle (θ, ϕ) indicating the display location of a target based on the horizontal angle θ and the vertical angle ϕ.

Figure 4:
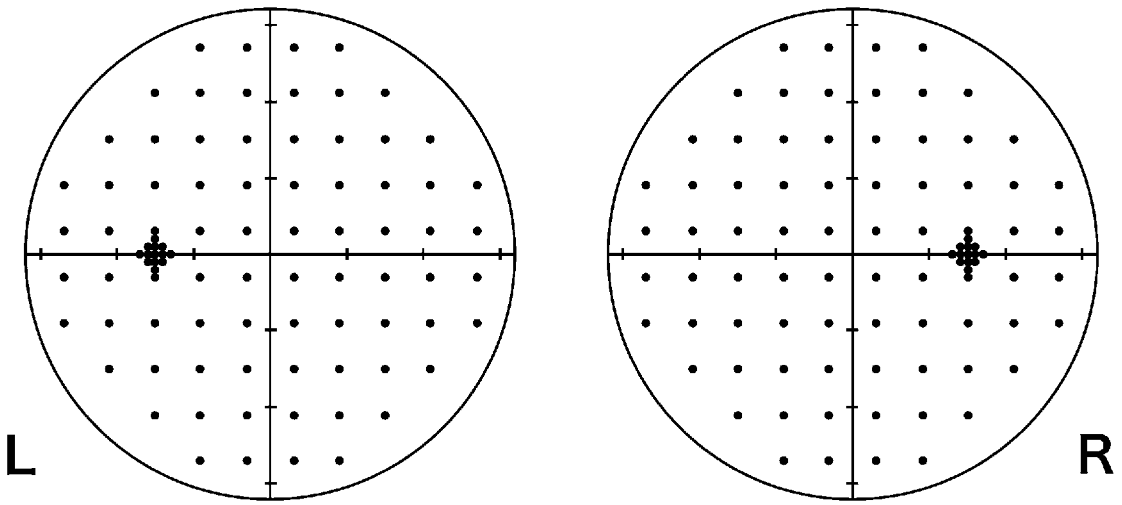
FIG. 4 is a drawing showing locations at which targets from a target display unit associated with an embodiment of the present invention might be displayed.

FIG. 4 shows display locations of targets that might be displayed at display 13, horizontal angles θ being plotted on the horizontal axis, and vertical angles ϕ being plotted on the vertical axis. Tick marks are shown on the respective axes for 10°, 20°, and 30°. When the user visually recognizes a target that is displayed at a location having a target angle (θ, ϕ), this constitutes a visual field angle (θ, ϕ). In accordance with the present embodiment, targets might be displayed within a visual field angle of 30°, for example, in both the horizontal direction and the vertical direction from such a location at front and center.

Note that when respective targets are displayed at display 13, target display unit 33 may, in accordance with the present embodiment, cause a target to be displayed at a location in the plane of display 13 that is the extension of an imaginary line segment drawn so as to connect the origin and the target which is displayed at a target angle with polar coordinates centered on the eye of the user so as to cause the angle of the line of sight that exists at a time when the line of sight of the user arrives at the target and is visually recognized to be the same as the aforesaid target angle of said target.

Visual recognition determination unit 40 which comprises collision determination unit 41 may carry out determination as to whether or not the line of sight of the user has arrived at the target, i.e., whether or not the target has actually been visually recognized by the user, based on the line of sight detected by line of sight detection unit 31 and the coordinates of the target displayed at display 13.

Collision determination unit 41 may carry out determination as to whether or not the target has been visually recognized by the user based on whether or not an imaginary line that is an extension of a line of sight direction detected by line of sight detection unit 31 within a prescribed coordinate system would physically collide with the target in question. More specifically, in accordance with the present embodiment, a determination might be made by collision determination unit 41 that there has been a collision and that visual recognition has taken place if upon comparison of the line of sight angle detected by line of sight detection unit 31 and the target angle indicating the location of the target in question, the angular difference therebetween is within 2°, for example.

Note that it is also possible for visual recognition determination unit 40 to cause visual recognition determination to be carried out using logical determinative techniques that make use of logged line of sight information. For example, a constitution may be adopted in which visual recognition determination unit 40 causes logical determination of visual recognition to be carried out when the line of sight approaches the target in question and continues to be located (staring takes place) near said target.

Characteristic testing unit 50, which has functionality for testing various characteristics of a user who uses characteristic testing system 1, may comprise visibility determination unit 51, visual field testing unit 55, multiple target testing unit 60, mild cognitive impairment (MCI) testing unit 62, concentration testing unit 65, and/or psychogenic visual impairment testing unit 67.

Visibility determination unit 51, which comprises visibility determination region establishment unit 52, may carry out determination as to whether or not a target at a position other than a position at display 13 which is in the line of sight of the user has been seen by (has caught the eye of) the user, i.e., whether or not it is visible.

After the target has been displayed at display 13, visibility determination unit 51 may carry out visibility determination based on the arrival path which is the path taken by the line of sight, and/or the arrival time which is the time taken by the line of sight, in going from the position that the line of sight was in at the time that display occurred until it arrives at said target. Determination as to whether or not the line of sight of the user arrived at the target may be carried out by visual recognition determination unit 40.

Regarding the arrival path, visibility determination unit 51 may carry out determination as to whether or not the path (arrival path) taken by the line of sight in going from the position that the line of sight was in at the time that the target was displayed until it arrived at the target was within a prescribed visibility determination region X.

Figure 6:
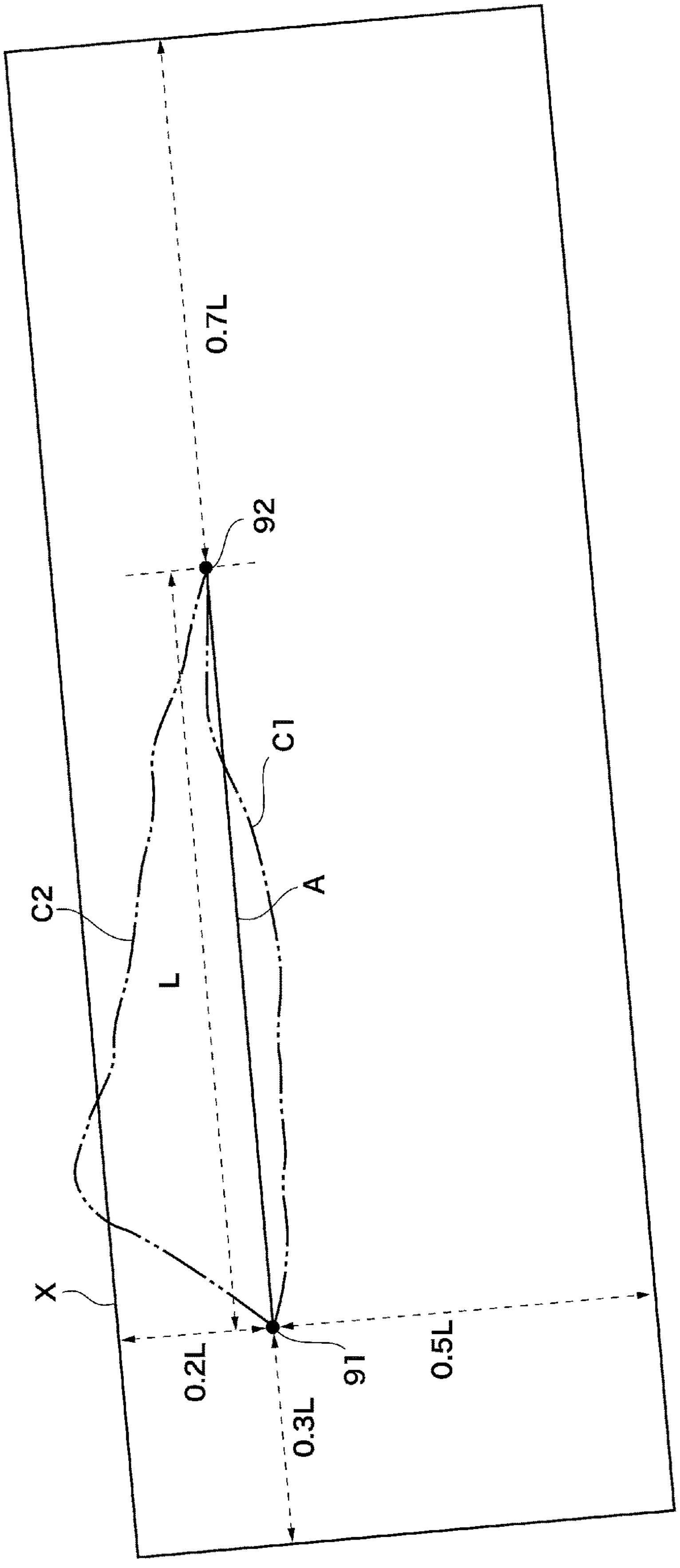
FIG. 6 is a drawing for describing a visibility determination region associated with an embodiment of the present invention.

In accordance with the present embodiment, visibility determination region establishment unit 52 might establish such a visibility determination region X (see FIG. 6). In accordance with the present embodiment, taking a line segment which connects two points—these being the initial position 91 of the line of sight when a target is displayed and the position 92 at which said target is displayed—to be line segment A, visibility determination region establishment unit 52 might cause visibility determination region X to be established as a rectangle which contains line segment A at the interior thereof and which is such that the long sides thereof are parallel to line segment A.

Describing this in further detail, taking the length of line segment A to be L, visibility determination region X might be established such that the distance between the initial position 91 of the line of sight and that short side of visibility determination region X which is toward the initial position 91 of the line of sight is 0.3 L, the distance between the position of target 92 and that short side thereof which is toward target 92 is 0.7 L, the distance between line segment A and that long side thereof which is to the right of the direction in which the line of sight proceeds in going from initial position 91 to target 92 is 0.5 L, and the distance between line segment A and that long side thereof which is to the left of the direction in which the line of sight proceeds in going from initial position 91 to target 92 is 0.2 L. That is, a rectangular visibility determination region X might be established such that the lengths of the long sides thereof are 2 L, and the lengths of the short sides thereof are 0.7 L.

Note that the aforementioned visibility determination region X would be for the right eye; the extent thereof from the initial position of the line of sight to the target would be flipped horizontally if for the left eye. That is, in accordance with the present embodiment, visibility determination region X for the left eye would span a greater distance to the left of the direction in which the line of sight proceeds than it spans to the right of the direction in which the line of sight proceeds.

Regarding the arrival time, visibility determination unit 51 may carry out determination as to whether or not the arrival time t taken in going from the initial position 91 that the line of sight was in at the time that the target was displayed until it arrived at target 92 was not greater than 862 ms.

Figure 5:
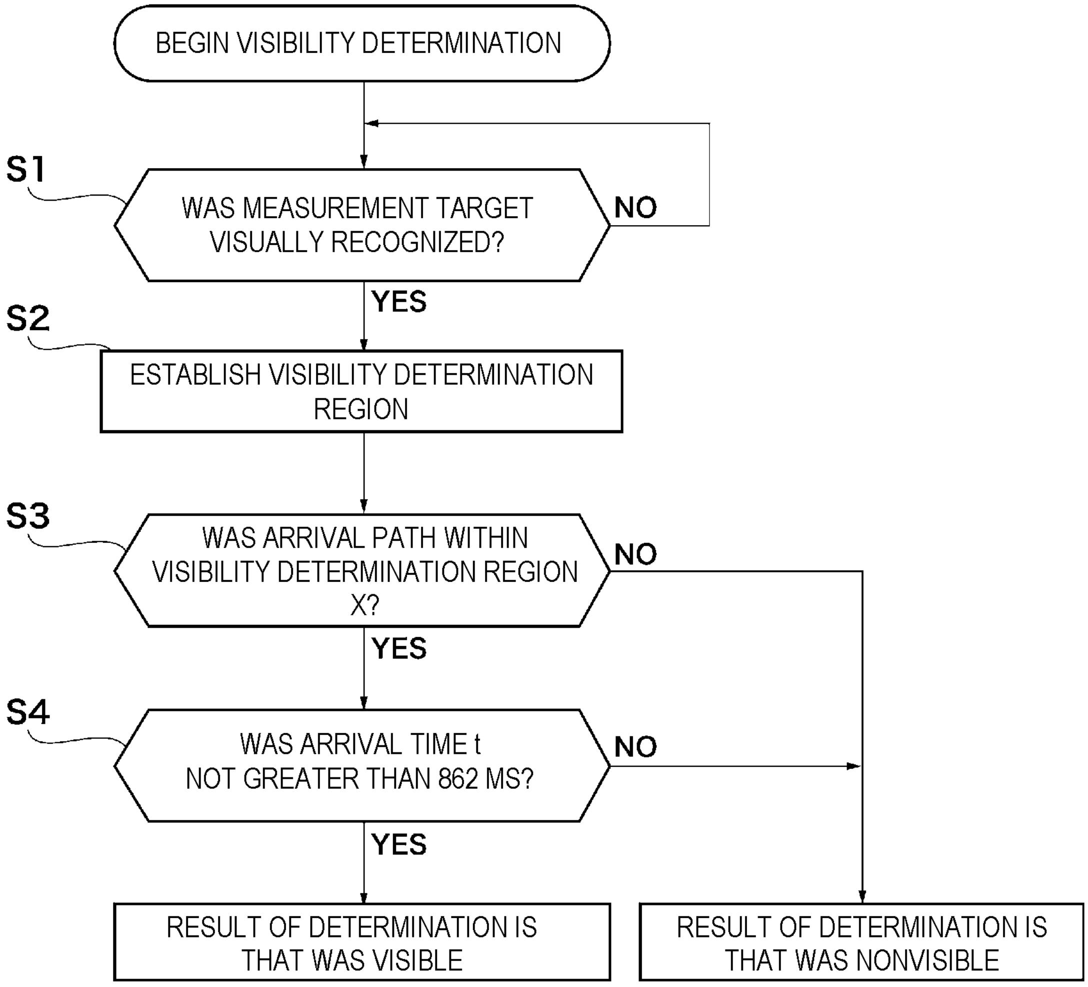
FIG. 5 is a flowchart showing flow of determination processing at a visibility determination unit associated with an embodiment of the present invention.

The flow of processing by which visibility determination might be carried out by visibility determination unit 51 in accordance with one embodiment will next be described with reference to FIG. 5. At S1, in accordance with the present embodiment, visibility determination unit 51 ascertains whether visual recognition determination unit 40 has determined whether or not target 92 was visually recognized by the user, processing proceeding to S2 if it was visually recognized.

At S2, in accordance with the present embodiment, visibility determination region establishment unit 52 establishes visibility determination region X; at S3, in accordance with the present embodiment, visibility determination unit 51 ascertains whether or not the arrival path C was within visibility determination region X. If this was within visibility determination region X (C1 at FIG. 6), processing would proceed to S4; if arrival path C passed outside of visibility determination region X (C2 at FIG. 6), determination would be made to the effect that said target 92 was nonvisible, and determination processing would terminate.

Upon processing having proceeded to S4, visibility determination unit 51 in accordance with the present embodiment ascertains whether or not the arrival time t was not greater than 862 ms. If this was not greater than 862 ms, determination would be made to the effect that said target 92 was visible; if the arrival time was greater than 862 ms, determination would be made to the effect that said target 92 was nonvisible, and determination processing would terminate.

During visibility determination, the reason that whether arrival path C was within visibility determination region X is ascertained in accordance with the present embodiment is because if this deviates greatly from the shortest possible path (line segment A) that could be taken by the line of sight in going from initial position 91 to the target 92, it is thought that this would likely have been due to the fact that presence of a scotoma at the time that the target was displayed prevented the user from seeing the target, and that it was only after the line of sight had been made to wander about that the target 92 happened to have been moved out of the scotoma and that this is what made it possible for the target 92 to have been seen somewhere along the way.

Furthermore, during visibility determination in accordance with the present embodiment, the reason that whether the arrival time t was not greater than a prescribed time is ascertained is because if the arrival time which is the time taken by the line of sight in going from initial position 91 to the target 92 is longer than a prescribed time, it is likewise thought that this would likely have been due to the fact that the user was unable to see the target 92 at the time that the target was displayed.

As described above, based on the arrival path which is the path taken by the line of sight, and/or the arrival time which is the time taken by the line of sight, in going from the initial position 91 of the line of sight at the time that the target was displayed until it arrived at the target 92, visibility determination unit 51 in accordance with the present embodiment may carry out determination to retroactively determine whether or not, at the time that a target was displayed, said target 92 was visible to the user.

Note that the shape and size of visibility determination region X, and the determination threshold (862 ms) for arrival time t, should preferably be established empirically based on historical measurement data, and may be varied as appropriate. For example, instead of being rectangular, the shape of visibility determination region X might be elliptical or in the shape of a polygon other than a rectangle, and the size thereof may be varied as appropriate.

Note, however, that it is preferred that visibility determination region X span a greater distance to the right of the direction in which the arrival path proceeds if for the right eye, and that it span a greater distance to the left of the direction in which the arrival path proceeds if for the left eye; and also that it span a greater distance in the direction in which the line of sight proceeds in going from the initial position 91 to the target 92 than it does in the reverse direction.

Furthermore, because it is preferred that the outer edge of visibility determination region X not be too far away from the shortest possible path (line segment A) that could be taken by the line of sight in going from initial position 91 to target 92, it is preferred that the size of visibility determination region X be such as to cause the outer edge of visibility determination region X to be located within distance L from line segment A.

Furthermore, whereas in accordance with the present embodiment visibility determination is carried out based on both the arrival path and the arrival time, visibility determination may be carried out based on one of either the arrival path or the arrival time.

In accordance with one embodiment, visual field testing unit 55 might control target display unit 33, visual recognition determination unit 40, and/or visibility determination unit 51, and might cause visual field testing of a user to be carried out by sequentially causing determination with respect to visibility of respective targets to be carried out by visibility determination unit 51 while causing targets for testing of visual field to be sequentially displayed at prescribed locations by target display unit 33.

As methods for causing targets to be displayed when visual field testing is carried out, target display unit 33 may be equipped with a mode employing two types of targets—these being gazing targets for causing the line of sight to return to the vicinity of a location at front and center with respect to which gazing (ocular fixation) is made to take place, and measurement targets for measuring visual field—and a mode that does not employ gazing targets but only employs measurement targets. In accordance with the present embodiment, visual field testing is fundamentally carried out in the mode that employs only measurement targets. Visual field testing may be carried out in accordance with Humphrey visual field testing (30-2 center) or the like.

Response testing in which multiple targets might be displayed by multiple target testing unit 60 will now be described. During processing by visibility determination unit 51, visual field testing unit 55, MCI testing unit 62, concentration testing unit 65, and/or psychogenic visual impairment testing unit 67, results of multiple target display response testing by this multiple target testing unit 60 may be employed for the purpose of improving the efficiency of the respective test(s).

Figure 7:
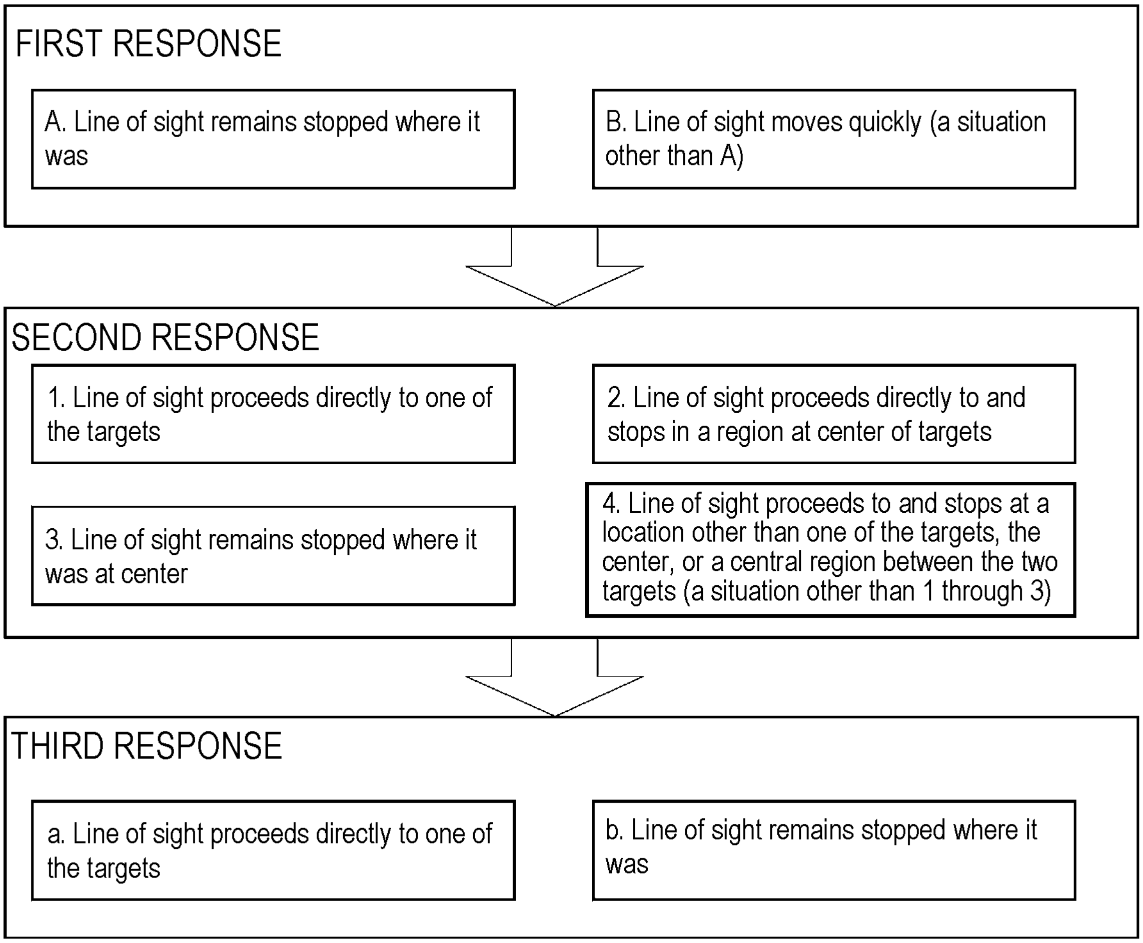
FIG. 7 is a flowchart showing flow of processing during response testing carried out by a multiple target testing unit associated with an embodiment of the present invention.

In accordance with the present embodiment, multiple target testing unit 60 may carry out testing with respect to the response of the line of sight of the user when two targets are simultaneously displayed at display 13, testing being carried out as a function of time in terms of a first response, second response, and third response as shown in FIG. 7, for example.

Figure 8:
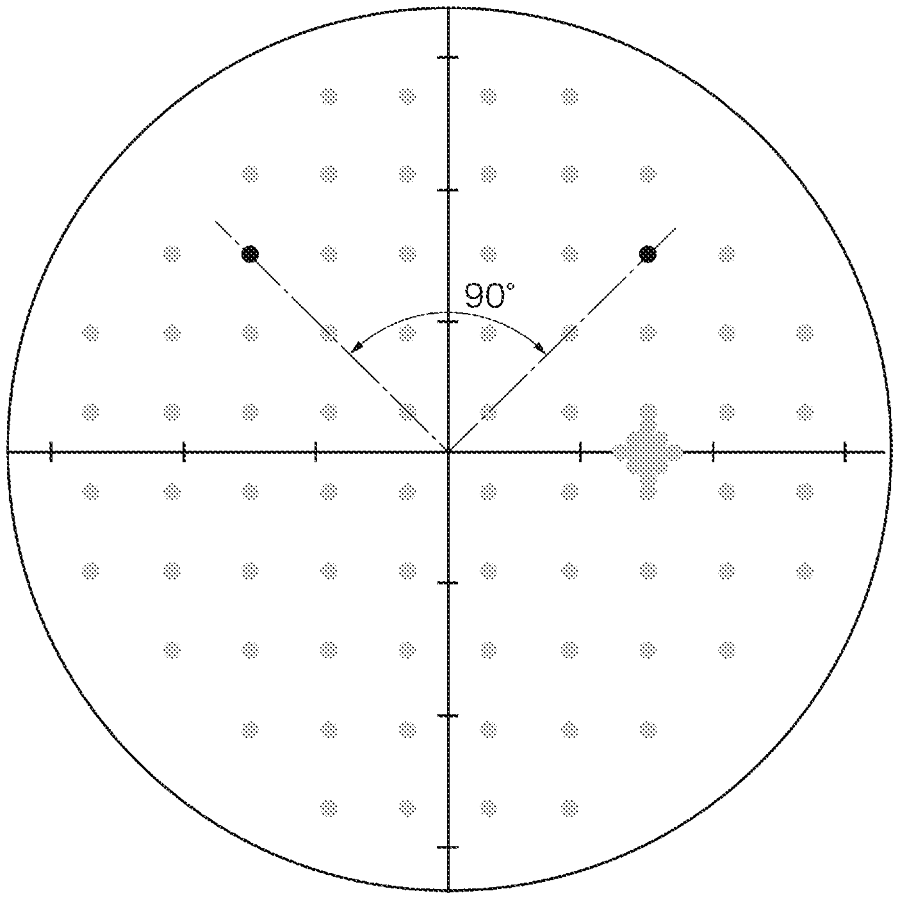
FIG. 8 is a drawing showing locations at which multiple targets might be displayed during multiple target display response testing associated with an embodiment of the present invention.

In accordance with the present embodiment, multiple target testing unit 60 might first cause two targets to be simultaneously displayed. FIG. 8 is a drawing showing locations at which two targets might be displayed during multiple target display response testing, display locations of targets being shown as target angles in a polar coordinate system in similar fashion as described above with reference to FIG. 4. At same drawing, dark black points indicate targets, and light gray points indicate locations at which targets are capable of being displayed, and the same thing is true with respect to FIG. 9.

In the present example, the two targets are equidistant, i.e., in terms of angular distance, from the location of the current line of sight, being displayed at locations 90° apart in a rotational direction centered on the location of the current line of sight at FIG. 8. Whereas the situation that exists when the line of sight is located at the central origin is shown by way of example at same drawing, even where the line of sight is at a location other than the origin, multiple target testing unit 60 may cause two targets to be displayed in similar fashion at locations that are equidistant (in terms of angular distance) and 90° apart in a rotational direction centered on the location of the current line of sight.

The display locations of the two targets may of course be varied as appropriate, it being possible depending on the testing which is being carried out that these need not be equidistant, i.e., in terms of angular distance, from the location of the current line of sight, nor that the rotational angle therebetween centered on the location of the current line of sight need be 90°. For example, in the example of psychogenic visual impairment determination which is described below, two targets at locations of differing distances from the location of the current line of sight are displayed. Note, however, that during visibility determination, described below, it is generally desirable that they be equidistant (in terms of angular distance).

After causing two targets to be simultaneously displayed, multiple target testing unit 60 might first carry out determination in connection with the first response. During the first response, multiple target testing unit 60 might carry out determination as to whether or not, immediately following display of targets, the line of sight remained stopped where it was at its original location. For example, this might be determined to be "A" if the line of sight remained stopped where it was; this might be determined to be "B" if it quickly began to move therefrom.

Here, determination with respect to staring, in which determination is made as to whether or not the line of sight remains stopped, i.e., determination as to whether or not the user continues to look in the vicinity of a prescribed coordinate location, might be carried out by determining that the user is staring at said coordinate location if, for example, the respective components of the most-recent prescribed number of (e.g., 15) sets of line of sight information recorded at line of sight log storage unit 76 are not greater than ±2° from the target angle of said coordinate location.

The method used to carry out determination with respect to staring may of course be varied as appropriate, it being possible, for example, to respectively calculate standard deviation(s) for the most-recent prescribed number of sets of line of sight information, and to determine that staring is taking place when value(s) of standard deviation(s) for all components are not greater than prescribed threshold value(s).

Following the first determination, a second determination might be carried out. During the second determination, when the line of sight proceeds directly to and then stops at either of the targets, this might be determined to be "1"; when the line of sight proceeds directly to and stops in the vicinity of a central location between the two targets, this might be determined to be "2"; when the line of sight does not move but remains stopped where it was at its original location, this might be determined to be "3"; and when something other than 1 through 3 occurs, this might be determined to be "4".

A "4" at the second response determination might, for example, be taken to mean that the line of sight stops at a location other than the two targets, midway between the two targets, or the initial position. Note that the line of sight ordinarily does not keep moving forever but will stop somewhere after having had a chance to move. Furthermore, in the case of "1" or "2" at the second determination, determination as to whether or not the line of sight proceeds directly thereto may be carried out through visibility determination using visibility determination region X by the foregoing visibility determination unit 51.

Following the second determination, a third determination might be carried out. During the third determination, following the second determination, determination might be carried out as to whether or not the line of sight proceeds directly toward either target, this being determined to be "a" if it proceeds to either target, and this being determined to be "b" if it remains stopped where it was. Here as well, determination as to whether or not the line of sight proceeds directly thereto may be carried out through visibility determination using visibility determination region X by visibility determination unit 51.

At the first determination through the third determination described above, each determination might, for example, be carried out within 250 ms, meaning that the determination in each case would be that the line of sight remains stopped (i.e., a determination would be made that staring is taking place) if it remains stopped where it was despite passage of 250 ms following the start of the determination.

Description having been given with respect to the content of determinations that may be carried out by multiple target testing unit 60, description will now be given with respect to what respective combinations of results (the first determination, the second determination, and the third determination) obtained at the first through third determination might, for example, be understood to mean in terms of movement of the line of sight.

A, 1, a: There was a delay in initial movement, and both targets were visually recognized.

A, 1, b: There was a delay in initial movement, and one of the targets was seen.

A, 2, a: There was a delay in initial movement, there was anxiety regarding which target to look at, and one of the two was seen.

A, 2, b: There was a delay in initial movement, there was anxiety regarding which target to look at, but neither was seen.

A, 3, a: There was considerable delay in initial movement, and one of the targets was seen.

A, 3, b: Search was not attempted.

A, 4, a: There was a delay in initial movement, search was attempted, and one of the targets was seen.

A, 4, b: There was a delay in initial movement, search was initiated, but the attempt to search was abandoned.

B, 1, a: Both targets were quickly seen.

B, 1, b: One target was quickly seen.

B, 2, a: There was a quick response, there was anxiety regarding which target to look at, and one of the two was seen.

B, 2, b: There was a quick response, there was anxiety regarding which target to look at, but neither was seen.

B, 3, a: (Nonexistent combination)

B, 3, b: (Nonexistent combination)

B, 4, a: There was a quick response, search was attempted, and one of the targets was seen.

B, 4, b: There was a quick response, search was initiated, but the attempt to search was abandoned.

Various characteristics tests which might be performed by characteristic testing unit 50 using results of testing from multiple target testing unit 60 will be described next. Visibility determination carried out by visibility determination unit 51 will first be described. Based on the first determination and the second determination, visibility determination unit 51 might carry out determination as to whether or not both of the two targets displayed at locations other than the location of the line of sight are visible.

When the result of determination at multiple target testing unit 60 is response (A, 2) or response (B, 2), visibility determination unit 51 might determine that both of the two targets were visible at the time that the targets were displayed.

For example, this might be understood to indicate that at the time of termination of the second response the line of sight of the user had proceeded to a location midway between the two targets and had stopped there, it being thought that this was due to the fact that at the time that the targets were displayed both of the two targets were seen by the user, the fact that the line of sight was stopped midway between the two targets being thought to be a result of the user's having been unable to decide which to move the line of sight to.

As described above, determination as to whether or not a target was visible at the time that the target was displayed would normally be carried out by visibility determination unit 51 based on the assumption that the line of sight arrived at said target as determined by visual recognition determination unit 40, meaning that where two targets are displayed, it would not be possible to determine that both targets were visible unless the line of sight were made to arrive at both targets.

To address this, by using the result of determination at multiple target testing unit 60, it is possible in accordance with the present embodiment to simultaneously carry out visibility determination with respect to the two targets even when the line of sight has not been made to arrive at the targets, making it possible to dramatically reduce the time required to carry out visibility determination.

Furthermore, based on the first determination and the second determination, visibility determination unit 51 might carry out determination as to whether or not both of the two targets displayed at locations other than the location of the line of sight are nonvisible. When the result of determination at multiple target testing unit 60 is response (A, 4) or response (B, 4), visibility determination unit 51 might determine that both of the two targets were nonvisible at the time that the targets were displayed.

For example, this might be understood to indicate that at the time of termination of the second response the line of sight of the user had proceeded to a location that was neither the original location nor either of the targets nor a location midway between the two targets and had stopped there, it being thought that this was due to the fact that the line of sight had been moved to and made to stop at that other location due to the fact that neither of the two targets had been seen by the user. In such a situation as well, visibility determination unit 51 in accordance with the present embodiment will make it possible to dramatically reduce the time required to carry out visibility determination.

By making use of the visibility determination carried out by visibility determination unit 51, which thus causes simultaneous display of two targets and reduces determination time in accordance with the present embodiment, visual field testing unit 55 in accordance with the present embodiment may make it possible to achieve dramatic reduction in the time required to carry out visual field testing.

Testing of mild cognitive impairment which may be carried out by MCI testing unit 62 will be described next. During MCI testing, the user might, for example, be instructed to look at target(s) displayed at display 13. MCI testing unit 62 may be such that, for each determination result combination at multiple target testing unit 60, points (5 points being a perfect score) are assigned as described below, testing as to whether or not mild cognitive impairment exists being carried out based on the number of points, for example. Note, however, that during testing by MCI testing unit 62, determination with respect to staring at the first response by multiple target testing unit 60 in accordance with the present embodiment is preferably such that the determination with respect to staring is carried out based on whether or not the line of sight stops not for 250 ms but for three times this, i.e., 750 ms.

A, 1, a: 1
A, 1, b: 1
A, 2, a: 1
A, 2, b: 5
A, 3, a: 3
A, 3, b: 5
A, 4, a: 1
A, 4, b: 3
B, 1, a: 0
B, 1, b: 0
B, 2, a: 0
B, 2, b: 5
B, 4, a: 0
B, 4, b: 3

Because it is seen in academia that there is increase in initial movement time in senile patients, and because an "A" at the first response means that initial movement was delayed, points are added in accordance with the present embodiment for all such combinations. For example, in accordance with the present embodiment, a large number of points would be assigned for response (A, 3, b), as this is taken to mean that there is a strong suspicion that MCI exists, inasmuch as the instruction to search appears not to have been understood. Furthermore, in accordance with the present embodiment, a large number of points might be assigned for response (A, 2, b) and response (B, 2, b), inasmuch as neither target was seen despite the fact that both of the two targets were visible.

Furthermore, in accordance with the present embodiment, an intermediate number of points might be assigned for response (A, 3, a), because the response was too slow. For response (A, 4, b) and response (B, 4, b), while searching for targets was not performed, considering that this may have been due to the influence of fatigue, an intermediate number of points might, for example, be assigned.

MCI testing unit 62 might, for example, be such that testing by multiple target testing unit 60 is carried out multiple times, a determination being made that there is a suspicion that MCI exists if the cumulative number of points is greater than or equal to 0.8× the number of times that testing was carried out, for example. For example, if testing by multiple target testing unit 60 is carried out 20 times, and the total number of points is greater than or equal to 16 points, MCI testing unit 62 would, in accordance with the present embodiment, determine that there is a suspicion that MCI exists.

Second mild cognitive impairment testing at MCI testing unit 62 will be described next. During this testing, two targets of differing color might be displayed at display 13, and the user might be instructed to look at that of one color. For example, two targets might be respectively displayed in red and blue, and the user might be instructed to look at the target that is red.

In accordance with the present embodiment, MCI testing unit 62 may be such that, during second mild cognitive impairment testing as well, for each determination result combination at multiple target testing unit 60, points (5 points being a perfect score) are assigned as described below, testing as to whether or not mild cognitive impairment exists being carried out based on the number of points.

A, 1, a: 1 if the red target is ultimately looked at; 5 if the blue target is ultimately looked at
A, 1, b: 1 if the red target is ultimately looked at; 5 if the blue target is ultimately looked at
A, 2, a: 1 if the red target is ultimately looked at; 5 if the blue target is ultimately looked at
A, 2, b: 5 A, 3, a: 3 if the red target is ultimately looked at; 5 if the blue target is ultimately looked at
A, 3, b: 5 A, 4, a: 1 if the red target is ultimately looked at; 5 if the blue target is ultimately looked at
A, 4, b: 3 B, 1, a: 0 if the red target is ultimately looked at; 5 if the blue target is ultimately looked at
B, 1, b: 0 if the red target is ultimately looked at; 5 if the blue target is ultimately looked at
B, 2, a: 0 if the red target is ultimately looked at; 5 if the blue target is ultimately looked at
B, 2, b: 5 B, 4, a: 0 if the red target is ultimately looked at; 5 if the blue target is ultimately looked at
B, 4, b: 3

MCI testing unit 62 might be such that testing by multiple target testing unit 60 is carried out multiple times, a determination being made that there is a suspicion that MCI exists if the cumulative number of points is greater than or equal to 0.8× the number of times that testing was carried out, for example. While second mild cognitive impairment testing also provides similar action and effect as the foregoing mild cognitive impairment testing, because a large number of points are assigned for the respective determination results in accordance with the present embodiment, this makes it possible to carry out testing in a shorter period of time.

Concentration testing carried out by concentration testing unit 65 will be described next. During concentration testing, the user might be instructed to, as quickly as possible, look at target(s) displayed at display 13. Concentration testing unit 65 might be such that, for each determination result combination at multiple target testing unit 60, points (5 points being a perfect score) are assigned as described below, testing as to whether or not the user is able to concentrate being carried out based on the number of points.

A, 1, a: 3
A, 1, b: 3
A, 2, a: 3
A, 2, b: 0
A, 3, a: 1
A, 3, b: 0
A, 4, a: 3
A, 4, b: 0
B, 1, a: 5
B, 1, b: 5
B, 2, a: 5
B, 2, b: 0
B, 4, a: 5
B, 4, b: 0

Concentration testing unit 65 might be such that testing by multiple target testing unit 60 is carried out multiple times, a determination being made that concentration was possible if the cumulative number of points is greater than or equal to 80% of a perfect score, for example. For example, if multiple target display response testing is carried out 20 times, and the cumulative number of points is greater than or equal to 80 points, a determination might be made in accordance with the present embodiment that concentration was possible.

Psychogenic visual impairment determination which may be carried out by psychogenic visual impairment testing unit 67 will be described next. During psychogenic visual impairment determination, the user might be instructed to look at both of two targets in sets of targets that are sequentially displayed at display 13.

Figure 9:
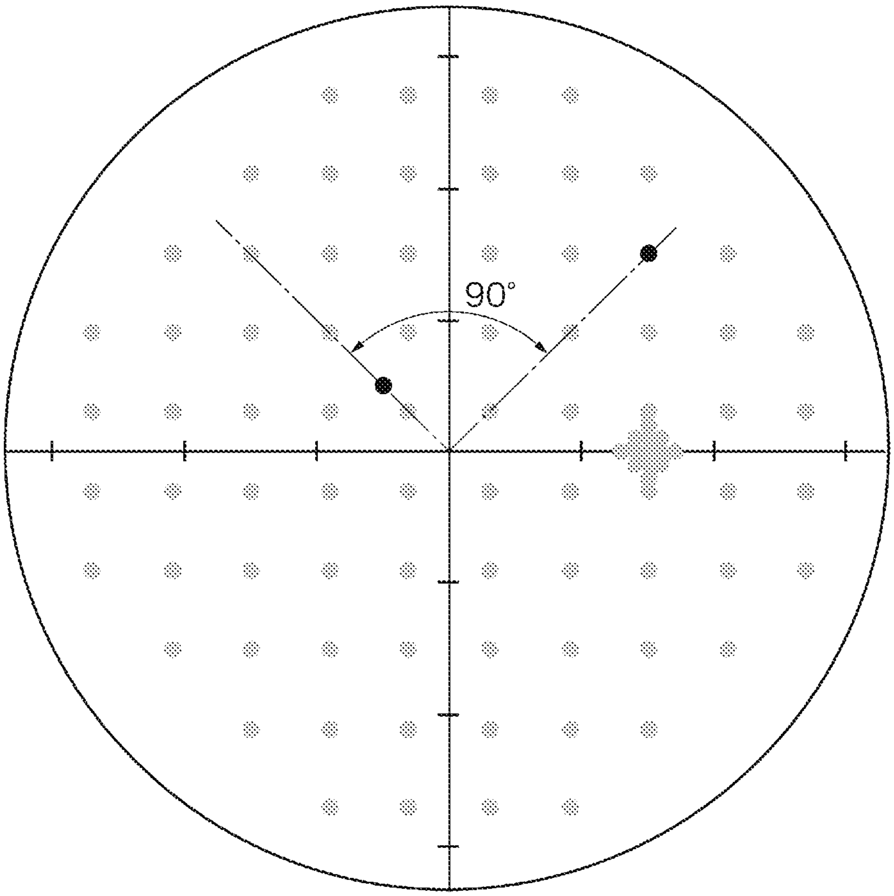
FIG. 9 is a drawing showing locations at which multiple targets might be displayed during psychogenic visual impairment testing associated with an embodiment of the present invention.

FIG. 9 shows locations at which two targets might be displayed during psychogenic visual impairment testing, in which multiple target testing unit 60, unlike the situation shown in the aforementioned FIG. 8, causes two targets to be simultaneously displayed at locations of differing distances from the location of the current line of sight.

More specifically, in accordance with the present embodiment, target display unit 33 might be controlled so as to cause one of the two targets (the inner target) to be displayed at a location at which the vertical angle and horizontal angle are both within 10° from a location at front and center which is the location of the current line of sight, and so as to cause the other target (the outer target) to be displayed at a location at which the vertical angle and horizontal angle are both not less than 20°. Furthermore, the two targets might be displayed at locations such as will cause the angle formed by lines respectively connecting the targets with the location of the current line of sight at front and center to be 90°.

Psychogenic visual impairment is a condition frequently found among children, in which visual acuity is reduced as a result of psychological stress. In accordance with the present embodiment, it might, for example, be assumed for a patient who has psychogenic visual impairment that as testing proceeds the visual field of the user will grow narrower and there will be increase in the frequency with which only the inner target is visually recognized.

In accordance with the present embodiment, first determination and second determination might be carried out multiple times by multiple target testing unit 60; and with respect to the second response, the number of times that the determination was "1" and the inner target was seen, the number of times that the determination was "1" and the outer target was seen, and the number of times that the determination was "2" might be counted, and the fractional number of times that the inner target was seen might be calculated.

Psychogenic visual impairment testing unit 67 might, for example, be such that 100 iterations of testing are carried out by multiple target testing unit 60, the determination being that there is a suspicion that psychogenic visual impairment exists if the fractional number of times that the inner target was seen during the final 50 iterations is greater than or equal to 1.5 times the fractional number of times that the inner target was seen during the initial 50 iterations, for example.

Above, description has been given with respect to characteristic testing system 1 associated with the present embodiment; in accordance with the present embodiment, by causing testing with respect to movement of the line of sight of a user at a time when two targets are displayed to be carried out by multiple target testing unit 60, it is possible for determination with respect to various characteristics of the user to be efficiently carried out by characteristic testing unit 50.

Moreover, the present invention is not limited to the foregoing embodiment but admits of any number of variations without departing from the gist of the present invention. For example, whereas a polar coordinate system was employed for lines of sight and line of sight position information at the foregoing embodiments, it is also possible to alternatively or additionally employ a three-dimensional rectangular coordinate system therefor.

Furthermore, whereas in the foregoing embodiments independent displays were used for the display for the left eye and the display for the right eye, it is also possible to use a single large display that has been divided into a region for the right eye and a region for the left eye.

Furthermore, whereas in the foregoing embodiments, testing with respect to movement of the line of sight of a user by the multiple target testing unit was carried out at a time when a plurality of targets in the form of two targets were simultaneously displayed, it is of course also possible to carry out testing with respect to movement of the line of sight of the user at a time when three or more targets are simultaneously displayed.

Where determination is carried out by the visibility determination unit at a time when three or more targets are simultaneously displayed, it will be possible to determine that all targets are visible when the line of sight of the user moves to and stops at a location midway thereamong which corresponds to a region at the center of the plurality of targets. Furthermore, it will likewise be possible to determine that all targets are nonvisible when the line of sight of the user proceeds to and stops at a location other than the initial position, any of the targets, or midway among the plurality of targets.

EXPLANATION OF REFERENCE NUMERALS

1 Characteristic testing system
10 HMD
11 Case
13 Display
14 Convex lens
15 Camera
16 Hot mirror
18 Emitter
30 Control apparatus
31 Line of sight detection unit

33 Target display unit
40 Visual recognition determination unit
41 Collision determination unit
50 Characteristic testing unit
51 Visibility determination unit
52 Visibility determination region establishment unit
55 Visual field testing unit
60 Multiple target testing unit
62 MCI (mild cognitive impairment) testing unit
65 Concentration testing unit
67 Psychogenic visual impairment testing unit
70 Arithmetic unit
75 Storage device
76 Line of sight log storage unit
77 Target storage unit
80 Cable
91 Initial position of line of sight
92 Target
A Line segment (shortest possible path)
C Arrival path
X Visibility determination region

What is claimed is:

1. A characteristic testing system that carries out testing of a characteristic of a user based on movement of a line of sight of the user, the characteristic testing system comprising:

- a line of sight detection unit that detects the line of sight of the user and that outputs line of sight information pertaining to direction of the line of sight;
- a target display unit that causes at least a first target and a second target to be displayed at a display;
- a visual recognition determination unit that carries out determination as to whether or not the user has visually recognized the first target based on the line of sight information and position information of the first target, and that carries out determination as to whether or not the user has visually recognized the second target based on the line of sight information and position information of the second target; and
- a characteristic testing unit that controls the target display unit and that carries out testing with respect to the characteristic of the user based on movement of the line of sight when at least the first target and the second target are displayed;
- wherein the characteristic testing unit comprises a multiple target testing unit that carries out testing with respect to the characteristic of the user when the first target and the second target are simultaneously displayed at the display;
- wherein the characteristic testing unit comprises a visibility determination unit that, when the first target and the second target are displayed at locations not in the line of sight when the first target and the second target were displayed, determines whether or not the first target and the second target were visible to the user; and
- wherein the visibility determination unit is such that, when the first target and the second target are simultaneously displayed pursuant to testing by the multiple target testing unit, determination is made that the first target and the second target were visible to the user if the line of sight proceeded to and stopped at a location midway between the first target and the second target.

2. The characteristic testing system according to claim 1 wherein the multiple target testing unit causes the first target and the second target to be simultaneously displayed at locations equidistant in terms of angular distance from the location of the line of sight when the first target and the second target are displayed.

3. The characteristic testing system according to claim 2 wherein the target display unit causes the first target and the second target to be displayed in respectively different colors.

4. The characteristic testing system according to claim 1 wherein the target display unit causes the first target and the second target to be displayed in respectively different colors.

5. A characteristic testing system that carries out testing of a characteristic of a user based on movement of a line of sight of the user, the characteristic testing system comprising:

- a line of sight detection unit that detects the line of sight of the user and that outputs line of sight information pertaining to direction of the line of sight;
- a target display unit that causes at least a first target and a second target to be displayed at a display;
- a visual recognition determination unit that carries out determination as to whether or not the user has visually recognized the first target based on the line of sight information and position information of the first target, and that carries out determination as to whether or not the user has visually recognized the second target based on the line of sight information and position information of the second target; and
- a characteristic testing unit that controls the target display unit and that carries out testing with respect to the characteristic of the user based on movement of the line of sight when at least the first target and the second target are displayed;
- wherein the characteristic testing unit comprises a multiple target testing unit that carries out testing with respect to the characteristic of the user when the first target and the second target are simultaneously displayed at the display;
- wherein the characteristic testing unit comprises a visibility determination unit that, when the first target and the second target have been displayed at locations not in the line of sight when the first target and the second target were displayed, determines whether or not the first target and the second target were visible to the user; and
- wherein the visibility determination unit is such that, when the first target and the second target are simultaneously displayed pursuant to testing by the multiple target testing unit, determination is made that neither the first target nor the second target were visible to the user if the line of sight proceeds to and stops at a location which is neither an initial position of the line of sight when the first target and the second target were displayed, nor a location of the first target, nor a location of the second target, nor a location midway between the first target and the second target.

6. The characteristic testing system according to claim 5 wherein the target display unit causes the first target and the second target to be displayed in respectively different colors.

7. The characteristic testing system according to claim 5 wherein the multiple target testing unit causes the first target and the second target to be simultaneously displayed at locations equidistant in terms of angular distance from the location of the line of sight when the first target and the second target are displayed.

* * * * *